United States Patent
Kagawa et al.

(10) Patent No.: US 11,697,794 B2
(45) Date of Patent: Jul. 11, 2023

(54) METHOD FOR PRODUCING LAYERED CELL SHEET AND LAYERED CELL SHEET PRODUCED BY THE SAME

(71) Applicants: NIHON KOHDEN CORPORATION, Tokyo (JP); TOKYO WOMEN'S MEDICAL UNIVERSITY, Tokyo (JP)

(72) Inventors: Yuki Kagawa, Tokorozawa (JP); Tatsuya Shimizu, Tokyo (JP); Yuji Haraguchi, Tokyo (JP); Hirotsugu Kubo, Tokorozawa (JP)

(73) Assignees: NIHON KOHDEN CORPORATION, Tokyo (JP); TOKYO WOMEN'S MEDICAL UNIVERSITY, Tokyo (JP)

( * ) Notice: Subject to any disclaimer, the term of this patent is extended or adjusted under 35 U.S.C. 154(b) by 621 days.

(21) Appl. No.: 16/627,156

(22) PCT Filed: Jun. 28, 2018

(86) PCT No.: PCT/JP2018/024605
§ 371 (c)(1),
(2) Date: Dec. 27, 2019

(87) PCT Pub. No.: WO2019/004361
PCT Pub. Date: Jan. 3, 2019

(65) Prior Publication Data
US 2020/0140807 A1    May 7, 2020

(30) Foreign Application Priority Data
Jun. 29, 2017 (JP) .................. 2017-127873

(51) Int. Cl.
*C12N 5/00* (2006.01)
*C12N 5/077* (2010.01)

(52) U.S. Cl.
CPC ......... *C12N 5/0062* (2013.01); *C12N 5/0658* (2013.01); *C12N 2513/00* (2013.01); *C12N 2523/00* (2013.01)

(58) Field of Classification Search
CPC .................... C12N 5/0062; C12N 2523/00
See application file for complete search history.

(56) References Cited

U.S. PATENT DOCUMENTS

| 5,284,766 A | 2/1994 | Okano et al. |
| 2004/0009566 A1* | 1/2004 | Okano ............... A61L 27/3826 435/174 |
| 2013/0171213 A1 | 7/2013 | Sekine et al. |

FOREIGN PATENT DOCUMENTS

| EP | 2617 810 A1 | 7/2013 |
| JP | 2-211865 A | 8/1990 |
| WO | 2012/036224 A1 | 3/2012 |

OTHER PUBLICATIONS

Yuji Haraguchi et al., "Scaffold-free tissue engineering using cell sheet technology", Royal Society of Chemistry, RCS Adv., No. 2, 2012, pp. 2184-2190.
Akiyuki Hasegawa et al., "Rapid fabrication system for three-dimensional tissues using cell sheet engineering and centrifugation", Journal of Biomedical Materials Research, vol. 103A, Issue 12, Society for Biomaterials, Wiley Publications, XP055504173, Hoboken, NY, Dec. 1, 2015, pp. 3825-3833.
Yuji Haraguchi et al., "Three-Dimensional Human Cardiac Tissue Engineered by Centrifugation of Stacked Cell Sheets and Cross-Sectional Observation of Its Synchronous Beatings by Optical Coherence Tomography", BioMed Research International, vol. 2017, XP055504266, Jan. 1, 2017, pp. 1-8.
Ai Kushida et al., "Decrease in culture temperature releases monolayer endothelial cell sheets together with deposited fibronectin matrix from temperature-responsive culture surfaces", Journal of Biomedical Materials Research, vol. 45, No. 4, Wiley, New York, NY, XP001204072, Jun. 15, 1999, pp. 365-362.
Shinako Masuda et al., "Three-dimensional cardiac tissue fabrication based on cell sheet technology", Advanced Drug Delivery Reviews, vol. 96, Elsevier, XP029372126, Amsterdam, NL, May 14, 2015, pp. 103-109.
Tatsuya Shimizu et al., "Fabrication of Pulsatile Cardiac Tissue Grafts Using a Novel 3-Dimensional Cell Sheet Manipulation Technique and Temperature-Responsive Cell Culture Surfaces", Circulation Research, Grune and Stratton, vol. 90, No. 3, XP002285777, Baltimore, MD, Feb. 22, 2002, pp. 1-9.
International Search Report (PCT/ISA/210) dated Sep. 14, 2018, issued by the International Searching Authority in International Application No. PCT/JP2018/024605.
Written Opinion (PCT/ISA/237) dated Sep. 14, 2018, issued by the International Searching Authority in International Application No. PCT/JP2018/024605.
Communication dated Jun. 29, 2021 issued by the Japanese Intellectual Property Office in counterpart Japanese Application No. 2017-127873.
Akiyuki Hasegawa et al., "Cell sheet lamination method using centrifugal force", Civil Society of the Japan Regenerative Medical Society, vol. 15, 2016, 3 pages total.

(Continued)

*Primary Examiner* — Laura Schuberg
(74) *Attorney, Agent, or Firm* — Sughrue Mion, PLLC

(57) ABSTRACT

The present invention provides a method for swiftly producing a layered cell sheet that is non-invasively obtained and is utilizable for transplantation, etc., the method including (1) a step of applying a centrifugal force to a first cell sheet on a temperature-responsive culture surface for a predetermined time in a temperature range from a lower critical solution temperature of the temperature-responsive culture surface to 45° C., (2) a step of further placing a second cell sheet on the first cell sheet, and (3) a step of applying a centrifugal force to the first cell sheet and the second cell sheet on the temperature-responsive culture surface for a predetermined time in the temperature range from the lower critical solution temperature to 45° C.; and also provides a layered cell sheet obtained by the method.

12 Claims, 7 Drawing Sheets

(56) References Cited

OTHER PUBLICATIONS

Sekiya Sachiko et al., "The foundation of cell sheet technology and development for clinical application", The Chemical Times, 2016, 7 pages total, https://www.kanto.co.jp/dcms_media/other/backno8_pdf23.pdf.

"UpCell", CellSeed Inc., 2021, 8 pages total, https://www.cellseed.com/en/business/product/upcell.html.

* cited by examiner

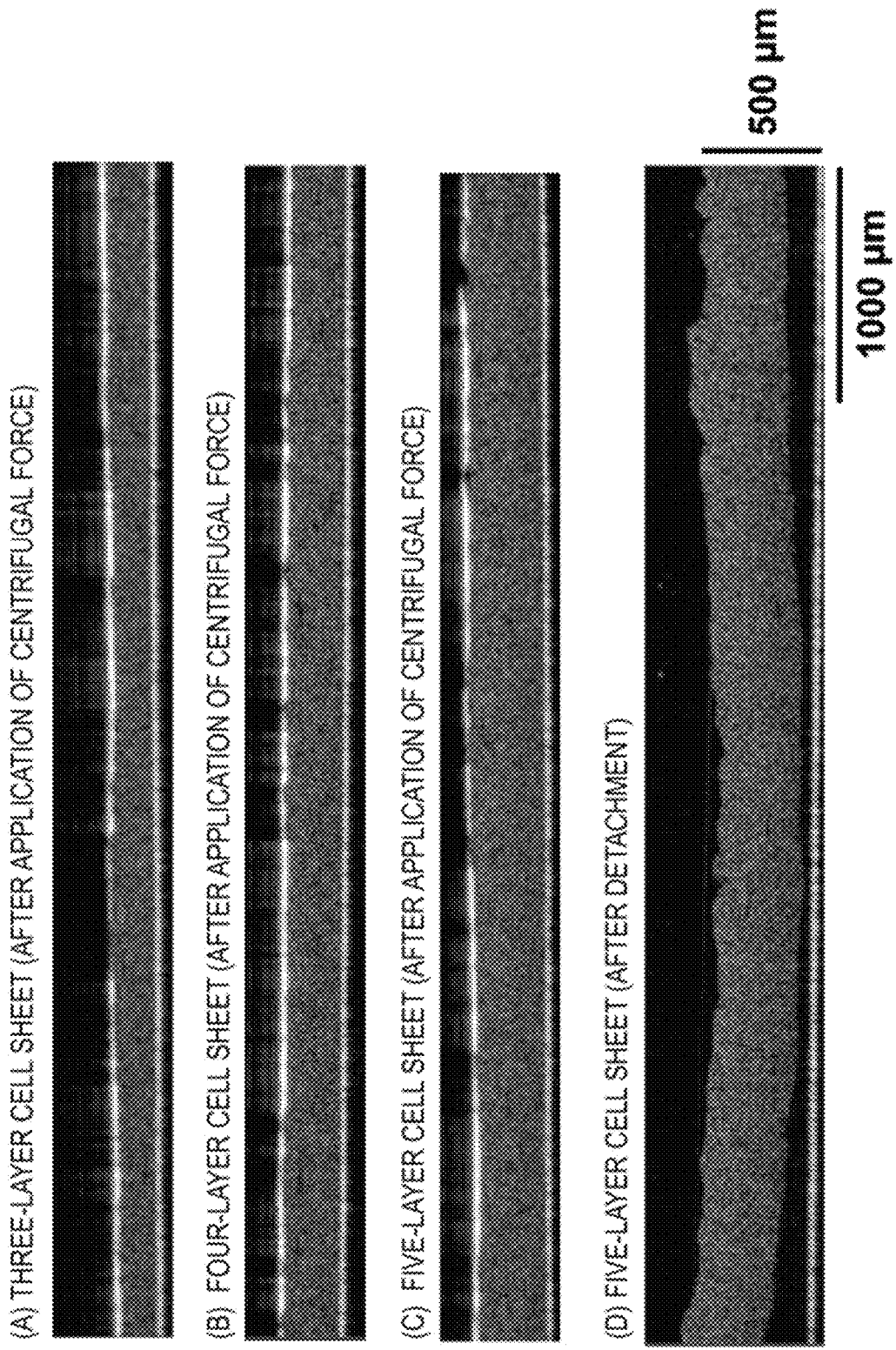

METHOD FOR PRODUCING LAYERED CELL SHEET AND LAYERED CELL SHEET PRODUCED BY THE SAME

TECHNICAL FIELD

The present invention relates to a method for producing a layered cell sheet. The present invention also relates to the layered cell sheet produced by the method for producing the layered cell sheet.

BACKGROUND ART

In recent years, a technique for manufacturing a three-dimensional tissue or organ using cells has been developed for utilizing it for tissue engineering or drug-responsive tissue models. Conventionally, many of adhesive cells could be cultured only two-dimensionally in vitro. However, many tissues of an organism are constructed by arranging cells three-dimensionally. For producing a tissue that is in a state close to the in vivo state, a technique for arranging cells three-dimensionally has been demanded.

Various attempts to arrange cells three-dimensionally have been developed such as a method of seeding cells on a three-dimensional structure called a scaffold, a method of decellularizing an organ or tissue and seeding cells on the remaining matrix to achieve three-dimensional arrangement, and a method of three-dimensionally layering cell sheets is released from in sheet form.

As one of the methods for producing a cell sheet, a method of using a cell culture dish (temperature-responsive culture dish) coated with poly(N-isopropylacrylamide) (PIPAAm) is known (Patent Document 1). Sheet-like cells (cell sheet) are non-invasively obtained by culturing arbitrary cells on the temperature-responsive culture dish coated with PIPAAm and after the cells get confluent, lowering the temperature to 20° C., which is less than 32° C. of a lower critical solution temperature (LCST) of PIPAAm.

In the cell sheet, adhesiveness of cells with each other and an extracellular matrix (ECM) is maintained, and a three-dimensional tissue can be produced by layering a plurality of cell sheets (Non-Patent Document 1). Since the three-dimensional tissue, which is composed of a plurality of cell sheets layered and produced on the temperature-responsive culture dish, can be non-invasively obtained by only dropping the temperature, adhesiveness of cells with each other and ECM are maintained. Therefore, the three-dimensional tissue is efficiently engrafted into the target damaged tissue at the time of transplantation to provide an effective treatment. However, it takes 30 to 60 minutes to layer a cell sheet once, and a technique for shorting the layering time has been demanded.

To meet this demand, a technique of shorting the layering time by applying a centrifugal force to the layered cell sheet by means of a centrifuge for plates has been recently developed (Non-Patent Documents 2 and 3).

RELATED ART

Patent Document

[Patent Document 1] JP-A-02-211865

Non-Patent Document

[Non-Patent Document 1] Haraguchi Y., et al., Scaffold-free tissue engineering using cell sheet technology. RSC Adv., 2012; 2:2184-2190

[Non-Patent Document 2] Hasegawa A., et al., Rapid fabrication system for three-dimensional tissues using cell sheet engineering and centrifugation. J. Biomed. Mater Res. A 2015; 103:3825-3833

[Non-Patent Document 3] Haraguchi Y., et al., Three-dimensional human cardiac tissue engineered by centrifugation of stacked cell sheets and cross-sectional observation of its synchronous beatings by optical coherence tomography. Biomed. Res. Int. 2017; 2017: 5341702

SUMMARY OF INVENTION

Problems to be Solved by the Invention

Since the method of layering cell sheets by applying a centrifugal force, which has been developed, is performed at room temperature (20-23° C.), only a normal cell culture dish can be used for the layering of cell sheets, and it was difficult to non-invasively obtain and transfer the layered cell sheet. Accordingly, an object of the present invention is to provide a method for rapidly producing a layered cell sheet that is easily obtained and maintains the desired shape. Another object is to provide a layered cell sheet obtained by the method.

Means for Solving the Problems

The present inventors have made researches and developments by conducting studies from various angles so as to solve the problem above. As a result, surprisingly, when an optimal centrifugal force is applied in a given temperature range, a three-dimensional tissue can be produced by rapidly layering a plurality of cell sheets on a temperature-responsive culture dish and moreover, the three-dimensional tissue can be non-invasively obtained by only dropping the temperature. Furthermore, the produced tissue obtained can be easily transferred to the target surface. That is, the present invention is as follows.

[1] A method for producing a layered cell sheet, the method comprising:

(1) a step of applying a centrifugal force to a first cell sheet on a temperature-responsive culture surface for a predetermined time in a temperature range from a lower critical solution temperature of the temperature-responsive culture surface to 45° C., (2) a step of further placing a second cell sheet on the first cell sheet, and (3) a step of applying a centrifugal force to the first cell sheet and the second cell sheet on the temperature-responsive culture surface for a predetermined time in the temperature range from the lower critical solution temperature to 45° C.

[2] The method according to [1], further comprising:

(4) a step of repeating the steps (2) and (3) an arbitrary number of times.

[3] The method according to [1] or [2], wherein the temperature-responsive culture surface is at least partially coated with poly(N-isopropylacrylamide).

[4] The method according to any one of [1] to [3], wherein the lower critical solution temperature is 32° C.

[5] The method according to any one of [1] to [4], wherein the temperature range is from 34 to 39° C.

[6] The method according to any one of [1] to [5], wherein the predetermined time is from 1 to 10 minutes.

[7] The method according to any one of [1] to [6], wherein the centrifugal force is from 25×g to 150×g.

[8] The method according to any one of [1] to [7], wherein a time until reaching the centrifugal force is from 15 to 60 seconds.

[9] The method according to any one of [1] to [8], wherein a time until ceasing the centrifugal force is from 15 to 60 seconds.

[10] The method according to any one of [1] to [9], wherein the first cell sheet and/or the second cell sheet contains one type of cells or two or more types of cells selected from the group consisting of cardiomyocytes, hepatocytes, fibroblasts, myoblasts, pancreatic cells, renal cells, vascular endothelial cells, and epithelial cells.

[11] The method according to any one of [1] to [10], further comprising:

(5) a step of releasing a layered cell sheet from the temperature-responsive culture surface by exposing the temperature-responsive culture surface to a temperature less than the lower critical solution temperature.

[12] A layered cell sheet obtained by the method according to any one of [1] to [11].

Effects of the Invention

The present invention simplifies the step of layering cell sheets, and can shorten the production time of a layered cell sheet. In addition, based on the present invention, the layered cell sheet maintaining the morphology can be obtained reproducibly, although a monolayer or layered cell sheet that is produced by conventional methods can hardly maintain its adhesiveness to a temperature-responsive culture dish. Furthermore, the present invention allows the layered cell sheet produced to be simply and non-invasively obtained. The layered cell sheet tissue obtained can also be swiftly transferred to the target surface by a commercially available cell sheet transfer device (Tadakuma K, et al., Biomaterials, 2013:34:9018-9025) (Funrukawakikou Co., Ltd., Niigata, Japan). This infers that the cell sheet tissue obtained non-invasively can be transplanted in the target tissue surface.

BRIEF DESCRIPTION OF THE DRAWINGS

FIG. 7 illustrates a cross-section of a multilayer C2C12 myoblast cell sheet on a temperature-responsive culture surface, which is observed by optical coherence tomography (OCT). (A) to (C): (A) A three-layer cell sheet, (B) a four-layer cell sheet, and (C) a five-layer cell sheet, after applying a centrifugal force (55×g, 5 minutes) at 36 to 37° C. (D) A five-layer cell sheet after releasing from the cell culture surface.

MODE FOR CARRYING OUT THE INVENTION

Figure 1:
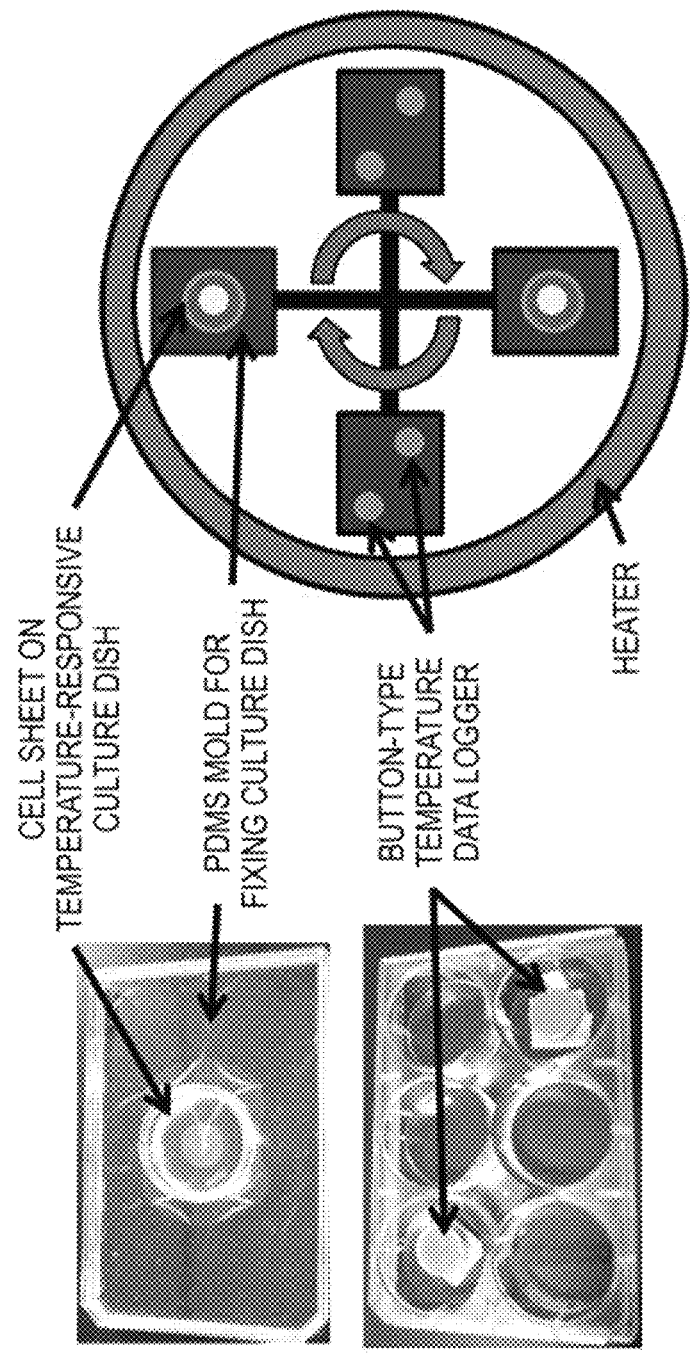
FIG. 1 illustrates a heated centrifuge for use in the present invention.

When cell sheets are layered using a normal centrifuge having no heating function and a temperature-responsive culture dish (for example, UpCell (registered trademark) (CellSeed Inc., Tokyo, Japan)), which has a cell non-adhesive surface at room temperature (20-23° C.), the cell sheet fails to adhere to the temperature-responsive culture dish and fails to be layered or arranged three-dimensionally. The present inventors have developed a centrifuge having a heating function and layered a plurality of cell sheets on the temperature-responsive culture dish using the centrifuge. As a result, the present inventors have succeeded not only in remarkably shortening the layering time but also in non-invasively releasing the layered cell sheet (three-dimensional tissue) from the temperature-responsive culture dish by only dropping the temperature.

That is, the present invention provides a method for producing a layered cell sheet, the method including:

(1) a step of applying a centrifugal force to a first cell sheet on a temperature-responsive culture surface for a predetermined time in a temperature range from a lower critical solution temperature of the temperature-responsive culture surface to 45° C., (2) a step of further placing a second cell sheet on the first cell sheet, and (3) a step of applying a centrifugal force to the first cell sheet and the second cell sheet on the temperature-responsive culture surface for a predetermined time in the temperature range from the lower critical solution temperature to 45° C.

In the present description, the "cell sheet" indicates a sheet-like cell aggregation that is formed at least in one layer on a cell culture surface and released from the cell culture surface.

The method for obtaining a cell sheet includes, but is not limited to, the following three methods. As the first method, firstly cells are cultured on a stimulus-responsive culture surface, which is coated with a polymer capable of changing the molecular structure in response to a stimulus such as temperature, pH, light and electricity, and secondly they are detached from the surface in a sheet form without breaking the cell-to-cell adhesion in response to the change in the culture surface, by varying the conditions of the stimulus such as temperature, pH, light and electricity. As the second method, cells are cultured on an arbitrary culture surface, and the cell aggregates cultured in a sheet form are physically peeled off by pulling the end of cell aggregates with a pair of tweezers or something like this. As the third method, cells are seeded on a culture surface with hydrogels or something, and the developed cell aggregates in a sheet form are detached from the surface.

In the present description, the "stimulus-responsive polymers" which cover a stimulus-responsive culture surface include but are not limited to poly(N-isopropylacrylamide), poly(N-isopropylacrylamide-acrylic acid) copolymer, poly(N-isopropylacrylamide-methyl methacrylate) copolymer, poly(N-isopropylacrylamide-sodium acrylate) copolymer, poly(N-isopropylacrylamide-vinylferroce) copolymer, γ ray-irradiated poly(vinyl methyl ether) (PVME), poly(oxyethylene), a resin prepared by incorporating a biomaterial such as nucleic acid into a polymer, and a gel prepared by crosslinking the above polymer with a crosslinking agent.

In the present description, the "temperature-responsive polymer" is one of stimulus-responsive polymers and indicates a polymer capable of changing its shape and/or property in response to temperature. The temperature-responsive polymers include but are not limited to poly(N-isopropylacrylamide), poly(N-isopropylacrylamide-acrylic acid) copolymer, poly(N-isopropylacrylamide-methyl methacrylate) copolymer, poly(N-isopropylacrylamido-sodium acrylate) copolymer, poly(N-isopropylacrylamide-vinylferrocene) copolymer, γ ray-iiradiated poly(vinyl methyl ether), and a gel prepared by crosslinking the above polymer with a crosslinking agent. Preferable polymers include but are not limited to poly(N-isopropylacrylamide), poly(N-isopropylacrylamide-methyl methacrylate) copolymer, poly(N-isopropylacrylamide-sodium acrylate) copolymer, and the gel prepared by crosslinking the above polymer with a crosslinking agent.

In the present description, the temperature-responsive polymers which coat the culture surface include, but are not limited to, those of which Upper Critical Solution Temperature (UCST) or Lower Critical Solution Temperature (LCST) is from 0 to 80° C. The critical solution temperature indicates a threshold temperature causing a change in the shape and/or property of the polymer. In the present invention, a cell culture surface which is at least partially coated with poly(N-isopropylacrylamide) (PIPAAm) may be preferably used.

The poly(N-isopropylacrylamide) (PIPAAm) is known as a polymer having a lower critical solution temperature (LCST) of 32° C. PIPAAm in a free state is dehydrated at a temperature of 32° C. or more in water and aggregates to become clouded. On the contrary PIPAAm is hydrated at a temperature of less than 32° C. and dissolved in water. The temperature-responsive culture surface used in one embodiment of the present invention is a culture surface such as petri dish in which PIPAAm coats and is fixed to the surface. Accordingly, at a temperature of 32° C. or more, PIPAAm on the culture surface is dehydrated similarly. PIPAAm is fixed to the culture surface, and the culture surface becomes hydrophobic. On the contrary, at a temperature of less than 32° C., PIPAAm on the culture surface is hydrated. PIPAAm coats the culture surface, and the culture surface becomes hydrophilic. Cells can adhere to the hydrophobic surface and grow, and cells are less likely to adhere to the hydrophilic surface. Accordingly, when the temperature-responsive culture surface is cooled to less than 32° C., the cells are detached from the culture surface. When cells are cultured until getting confluent over the entire culture surface, a cell sheet can be obtained by cooling the culture surface to less than 32° C.

The cell sheet can be obtained using the stimulus-responsive culture surface of one embodiment of the present invention without using a protease such as dispase and trypsin, which is commonly used for cell collection, and therefore, the lower surface (surface on the side in contact with the culture surface) of the cell sheet retains adhesion proteins in abundance and also maintains cell-to-cell desmosome structures. Such a cell sheet is suitable for attaching to an affected part in an organism and layering of a plurality of cell sheets.

In one embodiment of the present invention, the first cell sheet composing the lowermost layer of the layered cell sheet may be: (i) a cell sheet obtained by previously seeding and culturing cells on a temperature-responsive culture surface to be used in the step of applying a centrifugal force, and then lowering the temperature to less than the lower critical solution temperature; (ii) a cell sheet obtained by using a stimulus-responsive culture surface different from the temperature-responsive culture surface to be used in the step of applying a centrifugal force; (iii) a cell sheet obtained by seeding and culturing cells on an arbitrary culture surface, and then physically peeling off a sheet-like cell aggregation on the surface by pulling the end of cell aggregates with a pair of tweezers or something like this; or (iv) a cell sheet obtained by seeding cells together with hydrogels or something, and detached the developed sheet-like cell aggregation. Among these, (i) a cell sheet obtained by previously seeding and culturing cells on a temperature-responsive culture surface to be used in the step of applying a centrifugal force, and then lowering the temperature to less than the lower critical solution temperature, and (ii) a cell sheet obtained by using a stimulus-responsive culture surface different from the temperature-responsive culture surface to be used in the step of applying a centrifugal force, are preferred. In one embodiment of the present invention, in the case of using the cell sheet of (ii) as the first cell sheet, the cell sheet can be transferred by a known transfer method to the temperature-responsive culture surface to be used in the step of applying a centrifugal force.

In the present invention, the method for transferring the cell sheet to an arbitrary place includes but is not limited to a method in which a cell sheet floating in the culture medium is aspirated together with the culture medium by a pipette, etc. and the cell sheet with the culture medium is discharged in a separate place, thereby transferring the cell sheet (for example, Haraguchi Y., et al., Nat. Protoc., 2012; 7:850-858); and a method of transferring the cell sheet by a cell sheet transfer device (for example, Tadakuma K., et al., Biomaterials, 2013; 34:9018-9025).

In the present invention, the centrifuge used for applying a centrifugal force may be a centrifuge capable of applying a centrifugal force to a culture vessel and is preferably, but is not limited to, a swing-type plate centrifuge (for example, iSPIN-04-28 manufactured by RORZE Lifescience, Inc. (Ibaraki, Japan)). The rotor of the centrifuge used in the present invention is preferably a swing-type rotor. By using a swing-type rotor, the centrifugal force can be applied in the direction perpendicular to the culture surface to promote adhesion of cell sheets.

In the present invention, at the time of applying a centrifugal force, a warming device may be disposed on the periphery of the rotor of the centrifuge to keep the temperature range from the lower critical solution temperature of the temperature-responsive culture surface to 45° C., or the centrifuge itself may be disposed and used in a place at a temperature in the range from the lower critical solution temperature of the temperature-responsive culture surface to 45° C. Disposing the warming device on the periphery of the rotor of the centrifuge is preferable. The warming device is not particularly limited, but the example thereof includes a silicone rubber heater. The temperature on the periphery of the rotor can be measured using a known device for measuring the temperature. The measured temperature is preferably monitored in real time to prevent overheating or overcooling of the temperature-responsive culture surface. The heating device may be on/off controlled manually or automatically by using a feedback loop based on the temperature monitored in real time with a temperature measuring device.

In the present invention, the temperature at the time of applying a centrifugal force is in the temperature range from the lower critical solution temperature of the temperature-responsive culture surface to 45° C. and may be, for example, in a temperature range of 32° C.-45° C., 32° C.-44° C., 32° C.-43° C., 32° C.-42° C., 32° C.-41° C., 32° C.-40° C., 32° C.-39° C., 32° C.-38° C., 33° C.-45° C., 33° C.-44° C., 33° C.-43° C., 33° C.-42° C., 33° C.-41° C., 33° C.-40° C., 33° C.-39° C., 33° C.-38° C., 34° C.-45° C., 34° C.-44° C., 34° C.-43° C., 34° C.-42° C., 34° C.-41° C., 34° C.-40° C., 34° C.-39° C., 34° C.-38° C., 35° C.-45° C., 35° C.-44° C., 35° C.-43° C., 35° C.-42° C., 35° C.-41° C., 35° C.-40° C., 35° C.-39° C., or 35° C.-38° C. The temperature range is preferably 32° C.-42° C., more preferably 33° C.-41° C., still more preferably 34° C.-39° C., and most preferably 35° C.-38° C. When a centrifugal force is applied to the cell sheet in the above-described temperature range, an active adhesive activity by the cell itself is promoted while the temperature-responsive culture surface maintains hydrophobicity, and the adhesiveness to the culture surface or another cell sheet is more enhanced. Furthermore, the present invention can provide the cell sheet adhering to the culture surface or another cell sheet without losing its morphology, although the conventional method provides the cell sheet which is stretched and deformed in the horizontal direction by centrifugal force. In addition, the time required for layering cell sheets shortens. Above all, the present invention eliminates a step of separately performing incubation after a centrifugal force, which the conventional method requires, thereby reducing the risk of contamination.

In the present description, the centrifugal force can be expressed as "n×g" (n is an arbitrary number), and this means that the force is n times the gravitational acceleration of the Earth. In the present invention, the centrifugal force applied to the temperature-responsive culture surface may be sufficient if it is from 25×g to 150×g, and may be, for example, from 25×g to 130×g, from 25×g to 100×g, from 25×g to 80×g, from 25×g to 60×g, from 30×g to 150×g, from 30×g to 130×g, from 30×g to 100×g, from 30×g to 80×g, from 30×g to 60×g, from 35×g to 150×g, from 35×g to 130×g, from 35×g to 100×g, from 35×g to 80×g, from 35×g to 60×g, from 40×g to 150×g, from 40×g to 130×g, from 40×g to 100×g, from 40×g to 80×g, from 40×g to 60×g. In the present invention, the centrifugal force is preferably from 25×g to 150×g, more preferably from 30×g to 130×g, still more preferably from 35×g to 100×g, yet still more preferably from 35×g to 80×g, and most preferably from 40×g to 60×g. When the centrifugal force above is applied to the cell sheet, the adhesiveness to the culture surface or another cell sheet is enhanced, and the layering time can be shortened.

In the present invention, the rotational frequency (rpm) of the centrifuge for applying a centrifugal force is appropriately determined depending on the instrument to be used, a type of the rotor, a radius of the rotor and something like these. The rotational frequency (rpm) of the centrifuge which is necessary to apply the above centrifugal force can be converted from the value of centrifugal force by a method known to one skilled in the art.

In the present invention, the predetermined time at the time of applying a centrifugal force is the duration of maintaining the target centrifugal force and excludes the time until reaching the target centrifugal force and the time until ceasing the centrifugal force. In the present invention, the predetermined time may be sufficient if it is from 1 to 10 minutes, and may be, from 1 to 9 minutes, from 1 to 8 minutes, from 1 to 7 minutes, from 1 to 6 minutes, from 1 to 5 minutes, from 2 to 10 minutes, from 2 to 9 minutes, from 2 to 8 minutes, from 2 to 7 minutes, from 2 to 6 minutes, from 2 to 5 minutes, from 3 to 10 minutes, from 3 to 9 minutes, from 3 to 8 minutes, from 3 to 7 minutes, from 3 to 6 minutes, or from 3 to 5 minutes. The predetermined time is preferably from 1 to 8 minutes, more preferably from 2 to 7 minutes, still more preferably from 2 to 6 minutes, and most preferably from 3 to 5 minutes.

In the present description, the time until reaching the centrifugal force indicates a time required from a point when the rotor of the centrifuge starts rotating to a point when the target centrifugal force is reached. In the present invention, the time until reaching the centrifugal force may sufficient if it is from 15 to 60 seconds, and may be, for example, from 15 to 55 seconds, from 15 to 50 seconds, from 15 to 45 seconds, from 15 to 40 seconds, from 20 to 60 seconds, from 20 to 55 seconds, from 20 to 50 seconds, from 20 to 45 seconds, from 20 to 40 seconds, from 25 to 60 seconds, from 25 to 55 seconds, from 25 to 50 seconds, from 25 to 45 seconds, from 25 to 40 seconds, from 30 to 60 seconds, from 30 to 55 seconds, from 30 to 50 seconds, from 30 to 45 seconds, from 30 to 40 seconds, from 35 to 60 seconds, from 35 to 55 seconds, from 35 to 50 seconds, from 35 to 45 seconds, or from 35 to 40 seconds. The time until reaching the centrifugal force is preferably from 15 to 55 seconds, more preferably from to 50 seconds, still more preferably from 25 to 45 seconds, and most preferably from 35 to seconds. When the time until reaching the centrifugal force is the time above, the cell sheet can be prevented from slipping and/or significant deformation caused by acceleration of the centrifuge.

In the present description, the time until ceasing the centrifugal force indicates a time required from a point when the rotation of the rotor of the centrifuge producing the target centrifugal force starts decelerating to a point when the rotation of the rotor of the centrifuge stops. In the present invention, the time until ceasing the centrifugal force may be sufficient if it is from 15 to 60 seconds, and may be, for example, from 15 to 55 seconds, from 15 to 50 seconds, from 15 to 45 seconds, from 15 to 40 seconds, from 20 to 60 seconds, from 20 to 55 seconds, from 20 to 50 seconds, from 20 to 45 seconds, from 20 to 40 seconds, from 25 to 60 seconds, from 25 to 55 seconds, from 25 to 50 seconds, from 25 to 45 seconds, from 25 to 40 seconds, from 30 to 60 seconds, from 30 to 55 seconds, from 30 to 50 seconds, from 30 to 45 seconds, from 30 to 40 seconds, from 35 to 60 seconds, from 35 to 55 seconds, from 35 to 50 seconds, from 35 to 45 seconds, or from 35 to 40 seconds. The time until ceasing the centrifugal force is preferably from 15 to 55 seconds, more preferably from 20 to 50 seconds, still more preferably from 25 to 45 seconds, and most preferably from 35 to 40 seconds. When the time until ceasing the centrifugal force is the time above, the cell sheet can be prevented from slipping and/or significant deformation caused by deceleration of the centrifuge.

In the step of further placing a second cell sheet in the present invention, the method for placing a second cell sheet on the first cell sheet includes but is not limited to a method in which the cell sheet floating in the culture medium is aspirated together with the culture medium by a pipette, etc. and the cell sheet with the culture medium is discharged in a separate place, thereby transferring the cell sheet (for example, Haraguchi Y., et al., Nat. Protoc., 2012; 7:850-858).

Some cells can hardly adhere to the cell culture surface and in such a case, one of cell-adhesive proteins such as collagen, laminin, laminin 5, fibronectin and matrigel, or a mixture of two or more thereof may be applied onto the cell culture surface.

In the present invention, the number of cells seeded to produce the first cell sheet and/or the second cell sheet differs depending on the animal species or cell types but may be, from $0.3 \times 10^4$ to $10 \times 10^6$ cells/cm$^2$, from $0.5 \times 10^4$ to $8 \times 10^6$ cells/cm$^2$, or from $0.7 \times 10^4$ to $5 \times 10^6$ cells/cm$^2$. In the present invention, the cell sheet can be released and obtained from the temperature-responsive culture surface by raising the temperature of the culture surface in which cells are confluent or sub-confluent to the upper critical solution temperature of the coat polymer or more, or dropping the temperature to the lower critical solution temperature or less. At this time, the cell sheet can be produced in a culture medium or in other isotonic solution, and the alternatives may be selected according to the purpose. To more rapidly release and obtain the cell sheet with high efficiency, a method of lightly tapping or swinging the culture surface, a method of stirring the culture medium by a pipette, and a method of using a pair of tweezers may be employed individually or in combination. The culture conditions except for the temperature may follow conventional practice. For example, the culture medium may be a culture medium containing known serums such as fetal bovine serum (FBS), or a serum-free culture medium.

In the present invention, the stimulus-responsive culture surface and/or the temperature-responsive culture surface may be a culture surface of dish, multiwell plate, flask or flat membrane. The stimulus-responsive culture surface and/or the temperature-responsive culture surface may be a culture surface formed of glass, modified glass, compounds such as polystyrene, polymethyl methacrylate and polycarbonate, substances capable of imparting morphology in general, such as polymer compound other than those described above, ceramics, etc., which are usually used for cell culture.

In the present invention, the cell type and the number of cells, contained in the first cell sheet and the second cell sheet, the ratio thereof, etc. may be appropriately selected or adjusted according to usage. For example, in the case of aiming at a method for regenerating myocardial tissue or evaluating the myocardial function, the cells to be used include any one of myocardial cells, cardiac myoblasts, myoblasts, mesenchymal stem cells, vascular endothelial cells, vascular endothelial progenitor cells, fibroblasts, bone marrow-derived cells, and adipose-derived cells, and a mixture of two or more of these cells.

In the case of aiming at a method for regenerating hepatic tissue, producing artificial liver simulating hepatic tissue, or evaluating the hepatic tissue function, the cells to be used include any one of hepatic parenchymal cells (also called hepatocyte), sinusoidal endothelial cells, Kupffer cells, stellate cells, pit cells, biliary epithelial cells, vascular endothelial cells, vascular endothelial progenitor cells, fibroblasts, bone marrow-derived cells, adipose-derived cells, mesenchymal stem cells, and a mixture of two or more of these cells.

In the case of aiming at a method for regenerating renal tissue, producing artificial kidney simulating renal tissue, or evaluating the renal function, the cells to be used include any one of renal cells, granular cells, collecting duct epithelial cells, parietal epithelial cells, podocytes, mesangial cells, smooth muscle cells, renal tubular cells, interstitial cells, glomerular cells, vascular endothelial cells, vascular endothelial progenitor cells, fibroblasts, bone marrow-derived cells, adipose-derived cells, and mesenchymal stem cells, and a mixture of two or more of these cell.

In the case of aiming at a method for regenerating adrenal tissue, producing an artificial adrenal gland simulating adrenal gland, or evaluating the adrenal function, for example, the cells to be used includes any one of adrenomedullary cells, adrenal cortical cells, zona glomerulosa cells, zonal fasciculate cells, zona reticularis cells, vascular endothelial cells, vascular endothelial progenitor cells, fibroblast, bone marrow-derived cells, adipose-derived cells, and mesenchymal stem cells, and a mixture of two or more of these cell.

In the case of aiming at a method for regenerating skin or evaluating the skin function, the cells used include any one of epidermal keratinocytes, melanocytes, arrector pili muscle cells, hair follicle cells, vascular endothelial cells, vascular endothelial progenitor cells, fibroblast, bone marrow-derived cells, adipose-derived cells, and mesenchymal stem cells, and a mixture of two or more of these cell.

In the case of aiming at a method for regenerating mucosal tissue or evaluating the mucosal tissue function, cells harvested from a tissue constituting the mucous membrane may be used. The kind of the mucous membrane includes buccal mucosa, gastric mucosa, intestinal mucosa, olfactory epithelium, oral mucosa, uterine mucous membrane. The cells to be used include but are not limited to any one of cells harvested from the mucous tissue, and a mixture of two or more of the cells.

In the case of aiming at a method for regenerating pancreas, producing artificial pancreas simulating pancreas, or evaluating the diabetes treatment or pancreas function, the cells to be used include α cells, β cells, δ cells, PP cells, and pancreatic acinar cells (collectively referred to as pancreatic cell).

In addition, such cells may be differentiated cells derived from ES cell, iPS cell, Muse cell, mesenchymal stem cell, etc.

The cells to be used in the present invention may be cells obtained by cutting a biological tissue into small pieces. In this case, a lot of different cells are mixed in the biological tissue-derived cell. For example, in later-described Examples of the present invention, the cell sheet is produced using cardiomyocyte contained in a minced cardiac tissue of rat. Such a cell sheet contains cardiac tissue-derived fibroblast, parietal cell, vascular endothelial cell, etc., in addition to cardiomyocyte. Accordingly, depending on the purpose, a cell sorter or antibody may be used to remove unnecessary cells, or conversely, a required cell may be added.

In another embodiment of the present invention, (2) a step of further placing a second cell sheet on the first cell sheet, and (3) a step of applying a centrifugal force to the first cell sheet and the second cell sheet on the temperature-responsive culture surface for a predetermined time in a temperature range from the lower critical solution temperature to 45° C., may be repeated an arbitrary number of times. In this present description, "repeating the steps (2) and (3)" means repeating the step of further placing an additional cell sheet on the layered cell sheet and the step of applying a centrifugal force to the additional cell sheet and the layered cell sheet on the temperature-responsive culture surface for the predetermined time in a temperature range from the lower critical solution temperature to 45° C. When the steps (2) and (3) are repeated an arbitrary number of times, a layered cell sheet composition having a desired thickness can be obtained. Above all, since the present invention allows for shortening the layering time compared with the conventional method for layering cell sheets, the more the number of layering times increases, the more pronounced the effect of shortening becomes. The number of layering times may be appropriately changed according to the purpose, and the layering may be repeated, for example, twice, 3 times, 4 times, 5 times, 6 times, 7 times, 8 times, 9 times, 10 times, 15 times, 20 times, 25 times, 30 times, 35 times, 40 times, 45 times, 50 times, 60 times, 70 times, 80 times, 90 times, 100 times, or a larger number of times. In addition, one layer of cell sheet may be layered per one layering, or two or more layers may be layered per once. When two or more layers of cell sheet are layered per once, the layering time can be further shortened.

The layered cell sheet obtained by the method of the present invention can be released from the temperature-responsive culture surface without damage, by further conducting a step of releasing the layered cell sheet from the temperature-responsive culture surface by exposing the temperature-responsive culture surface to a temperature less than the lower critical solution temperature.

The layered cell sheet released can be transferred to an arbitrary place, for example, by a cell sheet transfer device, similarly to the above.

EXAMPLES

The present invention is described in greater detail below based on Examples, but the present invention is not limited thereto by any means.

1. Material and Method 1-1. Cell Culture and Preparation of Cell Sheet

C2C12 mouse myoblasts (Sumitomo Dainippon Pharma Co., Ltd., Osaka, Japan) were cultured in Dulbecco's modified Eagle medium (DMEM) (Sigma-Aldrich, St. Louis, Mo., USA) containing 10% fetal bovine serum (FBS) (Japan Bio Serum, Nagoya, Japan) and 1% penicillin/streptomycin (Invitrogen, Carlsbad, Calif., USA), in a $CO_2$ incubator (Panasonic Healthcare Co., Ltd., Tokyo, Japan) set at 37° C.

A C2C12 myoblast cell sheet was prepared using a temperature-responsive culture dish (UpCell (registered trademark)) (CellSeed Inc., Tokyo, Japan) of 35 mm in diameter and using another $CO_2$ incubator (Wakenyaku Co., Ltd., Kyoto, Japan) set at 20° C. in accordance with the previously-reported method (Haraguchi Y., et al., Nat. Protoc., 2012; 7:850-858; Haraguchi Y., et al., Methods Mol. Biol., 2014; 1181:139-155). Handling of the cell sheet on the temperature-responsive culture dish, including the layering operation, was performed on a heating plate (Tokai Hit Corporation, Shizuoka, Japan) set at 37° C.

The five-layer C2C12 myoblast three-dimensional tissue on the temperature-responsive culture dish was released from the surface using the $CO_2$ incubator set at 20° C., and the released cell sheet three-dimensional tissue was easily transferred from the culture dish surface to the target place using a transfer device (Furukawakikou Co., Ltd., Niigata, Japan). This suggests that the cell sheet three-dimensional tissue swiftly produced on a temperature-responsive culture surface using a centrifuge with a heating function can be non-invasively obtained by only dropping the temperature and the obtained three-dimensional tissue can be transplanted.

Photography or videography of the cell sheet was performed with a digital camera (GR DIGITAL III) (Ricoh Company, Ltd., Tokyo, Japan) and a digital video camera (Xacti) (Panasonic Corporation, Osaka, Japan). Cross-sectional observation of the cell sheet on the culturing surface was performed by optical coherence tomography (OCT) (IVS-2000) (Santec Corporation, Aichi, Japan). A moving image of cardiomyocyte was recorded at 35 frames/sec with OCT.

1-2. Application of Centrifugal Force by Heating Centrifuge

According to the method by Hasegawa et al. (Hasegawa A., et al., J. Biomed. Mater Res. A., 2015; 103:3825-3833), a device for fixing a temperature-responsive culture dish of 35 mm in diameter was made with a 6-well culture plate (Corning, N.Y., USA) lid and polydimethylsiloxane (PDMS) (Dow Corning Toray Co., Ltd., Tokyo, Japan), and the device was set on a rotor of a swing-type plate centrifuge (iSPIN-04-28) (RORZE Lifescience, Inc., Ibaraki, Japan) (FIG. 1). A heater (silicone rubber heater) (ThreeHigh Co., Ltd., Kanagawa, Japan) was set around the centrifuge (FIG. 1). A temperature controller (monoone-120) (ThreeHigh Co., Ltd.) equipped with a temperature sensor (type K thermocouple) (TH-8296-2, ThreeHigh Co., Ltd.) was introduced into the centrifuge and connected to the heater. In the process of applying a centrifugal force, the temperature was monitored in chronological order by four button-type temperature data loggers (SUPER-THERMOCHRON) (KN Laboratories, Inc., Osaka, Japan) set in two 6-well plates (FIG. 1). To prevent overheating or overcooling, the temperature was adjusted between 35 to 37° C. by the controller.

1-3. Mechanical Rotation Test for Quantitatively Evaluating Adhesion of C2C12 Myoblast Cell Sheet on Temperature-Responsive Culture Surface or Adhesion Between Two-Layer Cell Sheets The adhesiveness (i) between the temperature-responsive culture surface and the C2C12 myoblast cell sheet and (ii) between two-layer cell sheets was quantitatively evaluated by a modified method (mechanical rotation test) of Hasegawa et al. (Hasegawa A., et al., J. Biomed. Mater Res. A., 2015; 103:3825-3833).

The cell sheet was released from the culture surface, and the cooled culture medium was replaced by a separately prepared warmed culture medium (37° C.). To evaluate the adhesiveness of the cell sheet to the culture surface, the cell sheet was spread, and the culture medium was then removed using a micropipette (P-1000) (M & S Instruments Inc., Osaka, Japan). Subsequently, (i) centrifugal force application (centrifugation method) or (ii) incubation (conventional method) at 37° C. was conducted.

In order to evaluate the adhesiveness between two-layer cell sheets, the second cell sheet was spread in the same manner as above on the first cell sheet on a polystyrene culture dish (Corning, N.Y., USA), and the culture medium was removed using a micropipette. Thereafter, centrifugal force was applied (i) at room temperature (22-23° C.) or (ii) at 36-37° C. After these operations, 2 mL of a warmed culture medium (DMEM) (37° C.) containing 10% FBS and 1% penicillin/streptomycin was poured in the culture dish having the cell sheet, the culture dish was set on a heating plate (37° C.), and the heating plate was set in a rotary shaker (TAITEC Corporation, Saitama, Japan). The rotary shaker was rotated at 90 rpm for 2 minutes. The cell sheet and the culture surface were judged as adhering when the adhesiveness therebetween was maintained, and judged as not adhering when they were separated.

1-4. Measurements of Glucose Consumption, Productions of Lactate and Vascular Endothelial Growth Factor (VEGF), and Lactate Dehydrogenase (LDH) Release of C2C12 Myoblast Cell Sheet The conditioned medium used in the monolayer C2C12 myoblast cell sheet on the temperature-responsive culture surface of 35 mm in diameter, and the cell sheet-free culture medium were collected 16 hours after the culture. The glucose consumption, productions of lactate and VEGF, and LDH release of cell sheet were measured according to the method by Tadakuma et el. (Tadakuma K., et al., Biomaterials, 2013; 34:9018-9025).

The glucose consumption was calculated by subtracting the glucose concentration of the cell sheet-containing culture medium after the culture from the glucose concentration of the cell sheet-free culture medium after the culture. The values of lactate production, VEGF production and LDH release were calculated by subtracting respective background concentrations of the cell sheet-free culture medium after the culture from respective concentrations of the cell sheet-containing culture medium after the culture. The cell sheet sample which was subjected twice to freeze-thawing (−80° C.→37° C.) was used as a positive control for cell death in LDH release assay. In the freezing-thawing experiment, the cell sheet-free culture medium after conducting freezing thawing twice was used as the background.

1-5. Data Analysis

All data were expressed as mean±SD. Two groups were compared by performing unpaired Student's t-test, and a p value exceeding 0.05 was regarded as insignificant. The Tukey-Kramer test was used for comparison of a plurality of groups.

2. Results

Comparative Example 1: Centrifugal Force Application at Room Temperature

Figure 2:
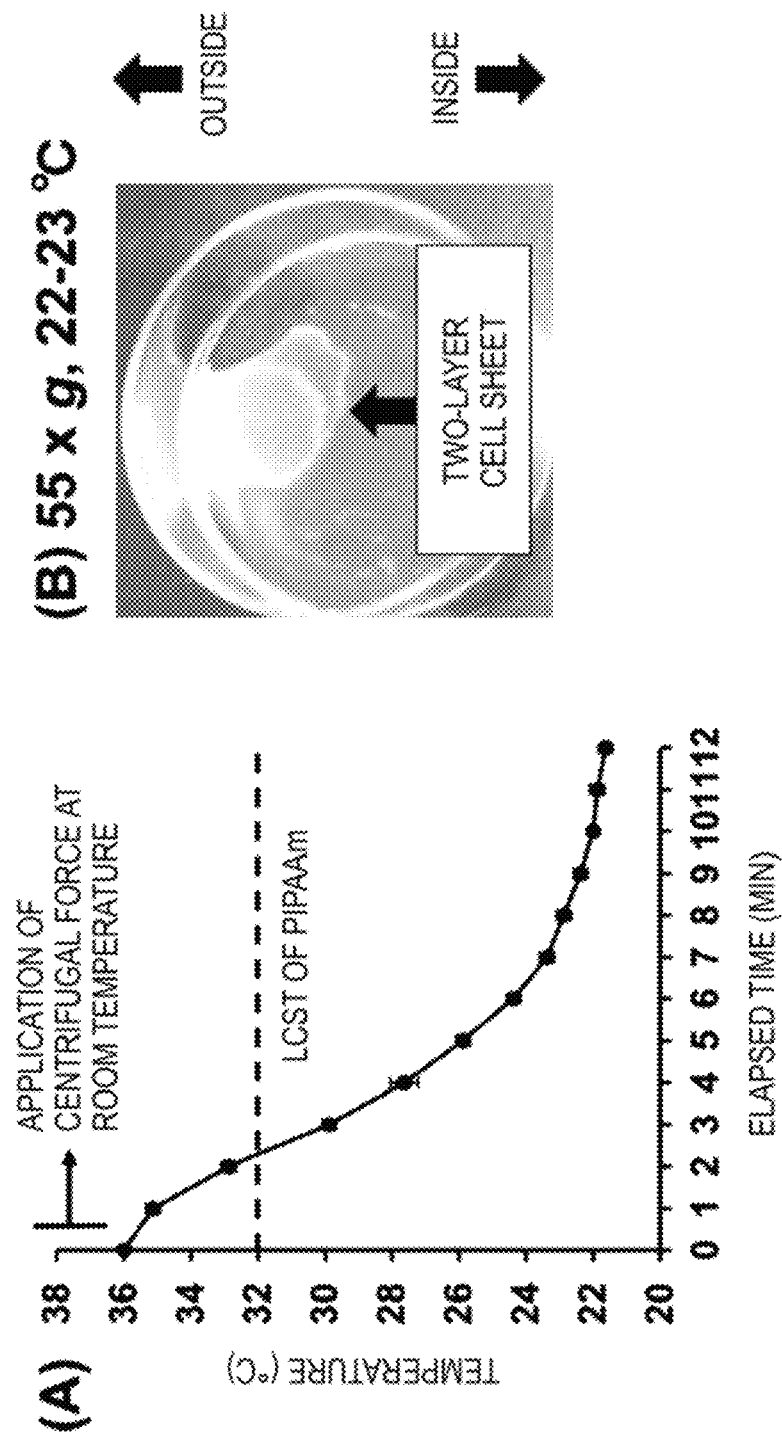
FIG. 2 illustrates a temperature change in the centrifuge having no heating function and an effect thereof on layered C2C12 myoblast cell sheets. (A) A graph illustrating the temperature change detected by four temperature sensors disposed in 6-well culture plate with mean±SD. When the centrifuge having no heater was used at room temperature, the temperature of the 6-well culture plate pre-warmed at 36 to 37° C. rapidly dropped. The dashed line indicates LCST of PIPAAm. (B) A photograph illustrating a two-layer cell sheet on a temperature-responsive culture dish after applying a centrifugal force (55×g, 5 minutes) at room temperature (22-23° C.).

The temperature on the periphery of the rotor of the centrifuge engaged in applying centrifugal force at room temperature (22-23° C.) was measured. The temperature of the 6-well plate pre-warmed by a $CO_2$ incubator at 37° C. rapidly lowered upon application of centrifugal force at room temperature (the part (A) of FIG. 2). As a result, it was revealed that even if the culture dish is pre-warmed, the temperature of the culture dish surface rapidly drops below LCST of PIPAAm by applying centrifugal force.

Figure 3:
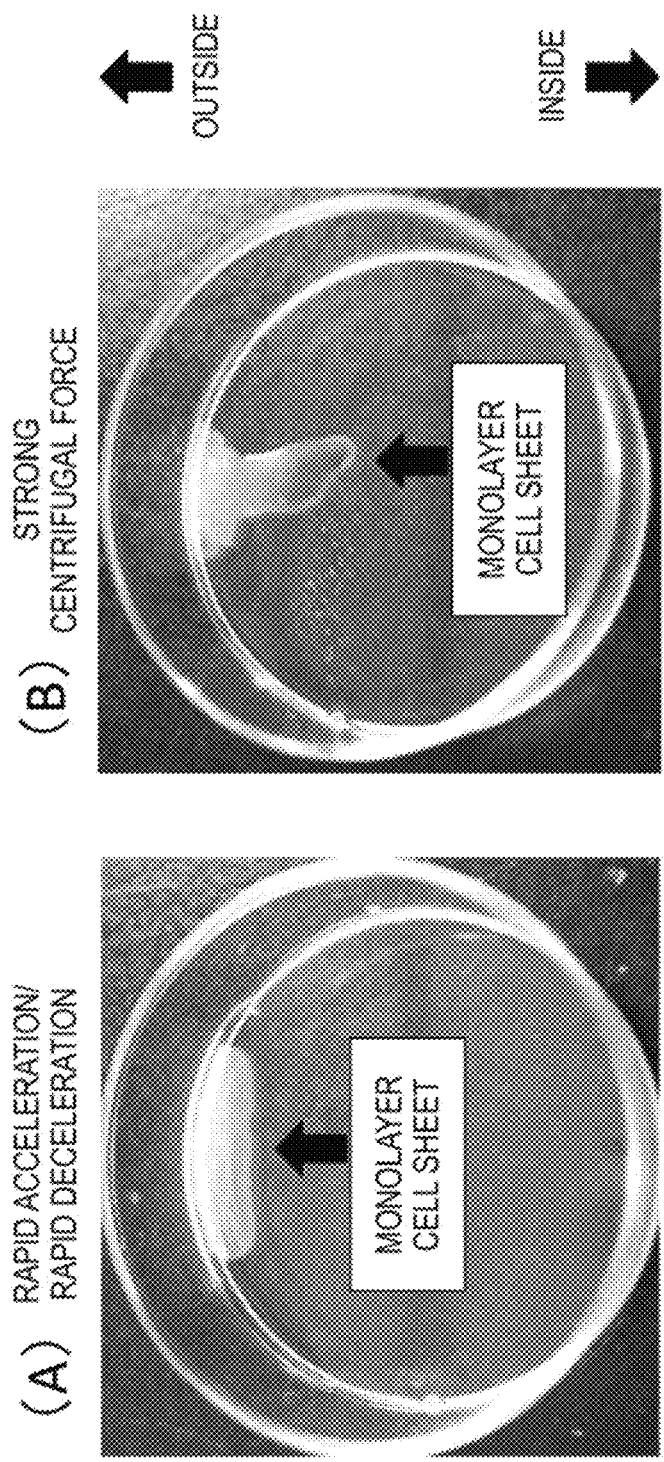
FIG. 3 illustrates a monolayer C2C12 myoblast cell sheet on a temperature-responsive culture dish. (A) and (B): Photographs illustrating a monolayer C2C12 myoblast cell sheet on a temperature-responsive culture dish (A) after a centrifugal treatment (55×g, 5 minutes) by rapid acceleration/deceleration (4 seconds until reaching the target speed) at room temperature (22-23° C.) or (B) after a high-speed centrifugal treatment (221×g, 5 minutes) at room temperature (22-23° C.).

C2C12 myoblast cells that were cultured on a temperature-responsive culture dish to be confluent was caused to spontaneously release as a cell sheet in a $CO_2$ incubator set at 20° C., and the released cell sheet was floated in a culture medium. According to the method by Haraguchi et al. (Haraguchi Y., et al., Nat. Protoc., 2012; 7:850-858), the cooled culture medium was replaced by a new warmed culture medium (37° C.), and the released cell sheet was spread by (i) rotation of culture dish, (ii) gentle dropping of culture medium, and/or (iii) gentle aspiration of culture medium. These operations were performed on a heating plate at 37° C. In order to adhere the released C2C12 myoblast cell sheet to the temperature-responsive culture surface, centrifugal force was applied. The warmed culture medium was removed, and centrifugal force was then applied at room temperature by placing the cell sheet-containing culture dish under three conditions (20×g, 55×g, and 221×g). In some cases, rapid acceleration and/or deceleration (when the time until reaching the target centrifugal force and/or the time until ceasing the centrifugal force is from 4 to 12 seconds) brought about an adverse effect such as sideslip or significant deformation of the cell sheet (the part of (A) of FIG. 3). Accordingly, a slow acceleration/deceleration (when the time until reaching the target centrifugal force and the time until ceasing the centrifugal force are 40 seconds) condition was used.

When weakest centrifugal force (20×g, 6 minutes) was applied, sideslip of the cell sheet was not detected in all of three tests. Immediately after centrifugal force application, a separately produced and released second cell sheet was obtained together with the warmed culture medium (37° C.) and transferred to the culture dish having a first cell sheet. For laying two cell sheets atop one another, as described above, the second cell sheet was spread on the first cell sheet (Haraguchi Y., et al., Nat. Protoc., 2012; 7:850-858). The operation was performed on a heating plate (37° C.). In the course of practicing these operations, in all of three tests, the first cell sheet substantially or completely detached from the surface, and the second cell sheet could not be layered on the first cell sheet.

Then, stronger centrifugal force (55×g, 5 minutes) was applied. In 6 runs out of 8 trial runs, the first cell sheet partially or completely detached from the culture dish surface in the course of practicing the operation of layering cell sheets. Furthermore, in some cases, significant deformation of the cell sheet was observed. When the application of centrifugal force was performed under the same centrifugal processing conditions, the cell sheets could be layered in 4 runs out of 8 trial runs. In one trial run out of these runs, sideslip of the cell sheet in the outside direction was observed (the part (B) of FIG. 2)

Next, strongest centrifugal force (221×g, 1 minute) was applied. In 2 trial runs under this condition of the centrifugal process, the cell sheet slid sideways to the end of the culture dish (the part (B) of FIG. 3). The slide direction was the outside direction when the culture dish was set on the rotor. It is considered that temperature drop during centrifugal force application under the heater-less condition poses weak adhesion between cell sheet and culture surface and causes sideslip, deformation or detachment of the cell sheet.

These results reveal that although optimization was attempted by changing the acceleration/deceleration or rotating speed, it is difficult to stably adhere the cell sheet to the temperature-responsive culture surface or layer the cell sheets and to rapidly produce a three-dimensional tissue on the temperature-responsive culture surface by applying centrifugal force at room temperature without heating.

Figure 4:
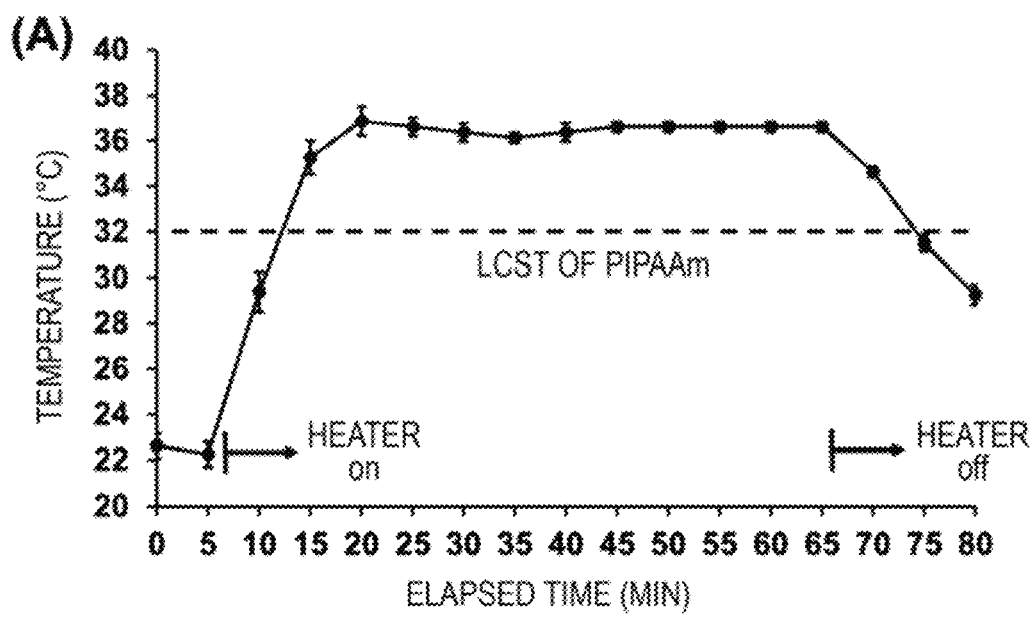
FIG. 4 illustrates a temperature change in the centrifuge having a heating function and an effect thereof on layered C2C12 myoblast cell sheets. (A) A graph illustrating the temperature change detected by four temperature sensors disposed in a 6-well culture plate with mean±SD. In the centrifuge having a heater, when the heater was turned on, the temperature around a rotor rapidly rose, and when the heater was turned off, the temperature around the rotor rapidly dropped. The dashed line indicates LCST of PIPAAm. (B) Photographs illustrating (B-1) a monolayer C2C12 myoblast cell sheet or (B-2) a two-layer C2C12 myoblast cell sheet, on a temperature-responsive culture dish after applying a centrifugal force (55×g, 5 minutes) at 36 to 37° C.
Figure 4:
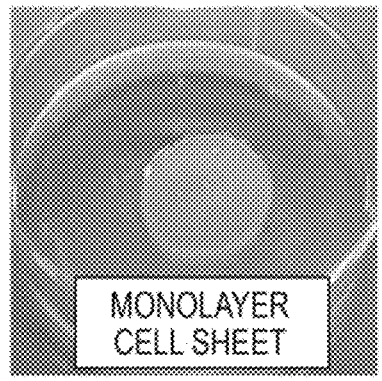
Figure 4:
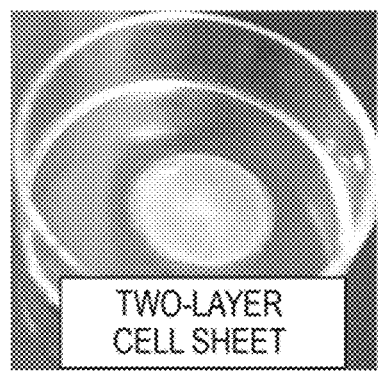

Example 1: Centrifugal Force Application by Centrifugal Processing Machine Having Heating Function To adhere a C2C12 myoblast cell sheet to a temperature-responsive culture surface at a temperature higher than LCST (32° C.) of PIPAAm, a centrifuge having a heating function was used. The temperature on the periphery of the rotor of the centrifugal processing machine engaged in applying centrifugal force rapidly rose when the heater was turned on, and rapidly dropped when the heater was turned off (the part (A) of FIG. 4). In this experiment, each of (i) opening/closing of the door of the centrifuge for setting a cell sheet sample and (ii) starting and ceasing of centrifugal force application, was performed three times. These operations did not greatly affect the temperature change, and a temperature exceeding LCST could be maintained. After the temperature was stabilized around 36 to 37° C., a temperature-responsive culture dish having a cell sheet was set, and centrifugal force was applied. The centrifugal force was applied in the temperature range of 36 to 37° C. under the same conditions (20×g, 55×g, and 221×g) as in the experiment at room temperature. In heating/centrifugal force application, it was observed that rapid acceleration and/or deceleration (when the time until reaching the target centrifugal force and/or the time until ceasing the centrifugal force is from 4 to 12 seconds) brings about a negative effect such as slipping or significant deformation of the cell sheet. Accordingly, mild acceleration/deceleration (when the time until reaching the target centrifugal force and the time until ceasing the centrifugal force are 40 seconds) was used also in this experiment.

When weakest centrifugal force (20×g, 6 minutes) was applied, the cell sheet adhered to the culture surface without sideslip. Immediately after centrifugal force application, the operation of layering the cell sheet was performed on a heating plate in the same manner as above. In 3 trial runs, adhesion between the first cell sheet and the culture surface was maintained, but in one trial run out of these runs, the cell sheet partially detached from the surface, revealing that the adherence by centrifugal force is slightly weak.

Then, stronger centrifugal force (55×g, 5 minutes) was applied. The cell sheet was adhering to the culture surface without sideslip (the part (B-1) of FIG. 4). During the operation of layering cell sheets, the adhesion between the first cell sheet and the culture surface was maintained in all of 5 trial runs. When the centrifugal force application to a two-layer cell sheet was performed under the same conditions, sideslip of the cell sheet layered was not detected in all of 5 tests (the part (B-2) of FIG. 4).

Next, strongest centrifugal force (221×g, 1 minute) was applied so as to shorten the centrifugal force application time. In 3 trial runs, the cell sheet slid sideways to the end of the culture dish, similarly to the centrifugal force application at room temperature.

These results reveal that when the centrifugal processing is performed at a temperature of 36 to 37° C. with heating and when optimal acceleration/deceleration or centrifugal speed is employed, the cell sheet can rapidly adhere to the temperature-responsive culture surface.

Example 2: Quantitative Evaluation of Adhesiveness Between C2C12 Myoblast Cell Sheet and Temperature-Responsive Culture Surface or Between Cell Sheets (Mechanical Rotation Test)

The adhesiveness of a C2C12 myoblast cell sheet to a temperature-responsive culture surface was quantitatively evaluated by a mechanical rotation test method (comparison with centrifugation method and conventional method). In the conventional method, after removing the culture medium, the culture was performed in the $CO_2$ incubator at 37° C. so as to promote the adhesion of the cell sheet to the culturing surface. A warmed culture medium (37° C.) was poured in the culture dish having the cell sheet 15 minutes after, 20 minutes after, or 25 minutes after the incubation, and the culture dish was set on a heating plate (37° C.) and rotated at 90 rpm with the rotary shaker. The adhesiveness of the cell sheet which was incubated for 25 minutes was maintained for 2 minutes in all of 3 trial runs, while the adhesiveness of the cell sheets which was incubated for 15 minutes and for 20 minutes could not be maintained (Table 1).

When centrifugal force (55×g) was applied at 36 to 37° C. for 3 minutes, the cell sheet maintained adhesion in 2 trial runs, but in one trial run, the cell sheet partially detached from the surface in 2 minutes after the rotation (Table 1). On the other hand, when centrifugal force was applied for 5 minutes, the cell sheet maintained adhesion for 2 minutes in all of 3 trial runs (Table 1), and it was proved that after applying centrifugal force for 5 minutes, the cell sheet firmly adheres to the culture surface. Centrifugal force application allowed for adhesion of the cell sheet and drastically shortening the adhesion time (⅕ (25 minutes→5 minutes)), compared with the conventional method without performing centrifugal processing.

TABLE 1

Evaluation of Adhesiveness Between C2C12 Myoblast Cell Sheet and Temperature-Responsive Culture Dish Adhesiveness Between Cell Sheet and Temperature-Responsive Culture Dish

| Incubation Time (min) | Centrifugal Force Application (3 minutes) | | | Centrifugal Force Application (5 minutes) | | | Conventional Method (non-centrifugation method) | | |
|---|---|---|---|---|---|---|---|---|---|
| 0 | adhered[*1] | adhered | partially detached[*2] | adhered | adhered | adhered | NT | NT | NT |
| 15 | NT[*3] | NT | NT | NT | NT | NT | completely detached[*4] | completely detached | completely detached |

TABLE 1-continued

Evaluation of Adhesiveness Between C2C12 Myoblast Cell Sheet and Temperature-Responsive Culture Dish
Adhesiveness Between Cell Sheet and Temperature-Responsive Culture Dish

| Incubation Time (min) | Centrifugal Force Application (3 minutes) | | | Centrifugal Force Application (5 minutes) | | | Conventional Method (non-centrifugation method) | | |
|---|---|---|---|---|---|---|---|---|---|
| 20 | NT | NT | NT | NT | NT | NT | adhered | completely detached | completely detached |
| 25 | NT | NT | NT | NT | NT | NT | adhered | adhered | adhered |

Adhered[*1]: The C2C12 myoblast cell sheet maintained adhesion to the temperature-responsive culture surface for 2 minutes.
Partially detached [*2]: The C2C12 myoblast cell sheet was partially detached from the temperature-responsive culture surface within 2 minutes.
NT[*3]: Not tested.
Completely detached[*4]: The C2C12 myoblast cell sheet was completely detached from the temperature-responsive culture surface within 2 minutes.

Next, the adhesiveness between two-layer C2C12 myoblast cell sheets was quantitatively evaluated by the mechanical rotation test (centrifugal force application at room temperature vs. centrifugal force application at 36-37° C.). In order to prevent the layered cell sheets from detachment and sideslip due to centrifugal force application at room temperature, two cell sheets were layered on a polystyrene culture dish, and centrifugal force (55×g) was applied to the layered cell sheets at room temperature of at 36-37° C. It was proved that in centrifugal force application for 2 to 4 minutes, the adhesion between cell sheets at 36 to 37° C. tends to be stronger than the adhesion at room temperature (Table 2), and in heating/centrifugal force application, strong adhesion between layered cell sheets is rapidly achieved compared with centrifugal processing at room temperature not performing heating treatment (Table 2).

TABLE 2

Evaluation of Adhesiveness Between Two-Layer C2C12 Myoblast Cell Sheets
Adhesiveness Between Cell Sheets

| Temperature | Centrifugal Force Application (2 minutes) | | | Centrifugal Force Application (3 minutes) | | | Centrifugal Force Application (4 minutes) | | |
|---|---|---|---|---|---|---|---|---|---|
| 22 to 23° C. | completely detached[*1] | partially detached[*2] | partially detached | adhered | partially detached | partially detached | adhered | adhered | adhered |
| 36 to 37° C. | partially detached | partially detached | adhered[*3] | adhered | adhered | adhered | adhered | adhered | adhered |

Completely detached[*1]: The C2C12 myoblast cell sheet was completely detached from another cell sheet within 2 minutes.
Partially detached[*2]: The C2C12 myoblast cell sheet was partially detached from another cell sheet within 2 minutes.
Adhered[*3]: The C2C12 myoblast cell sheet maintained adhesion to another cell sheet for 2 minutes.

Figure 5:
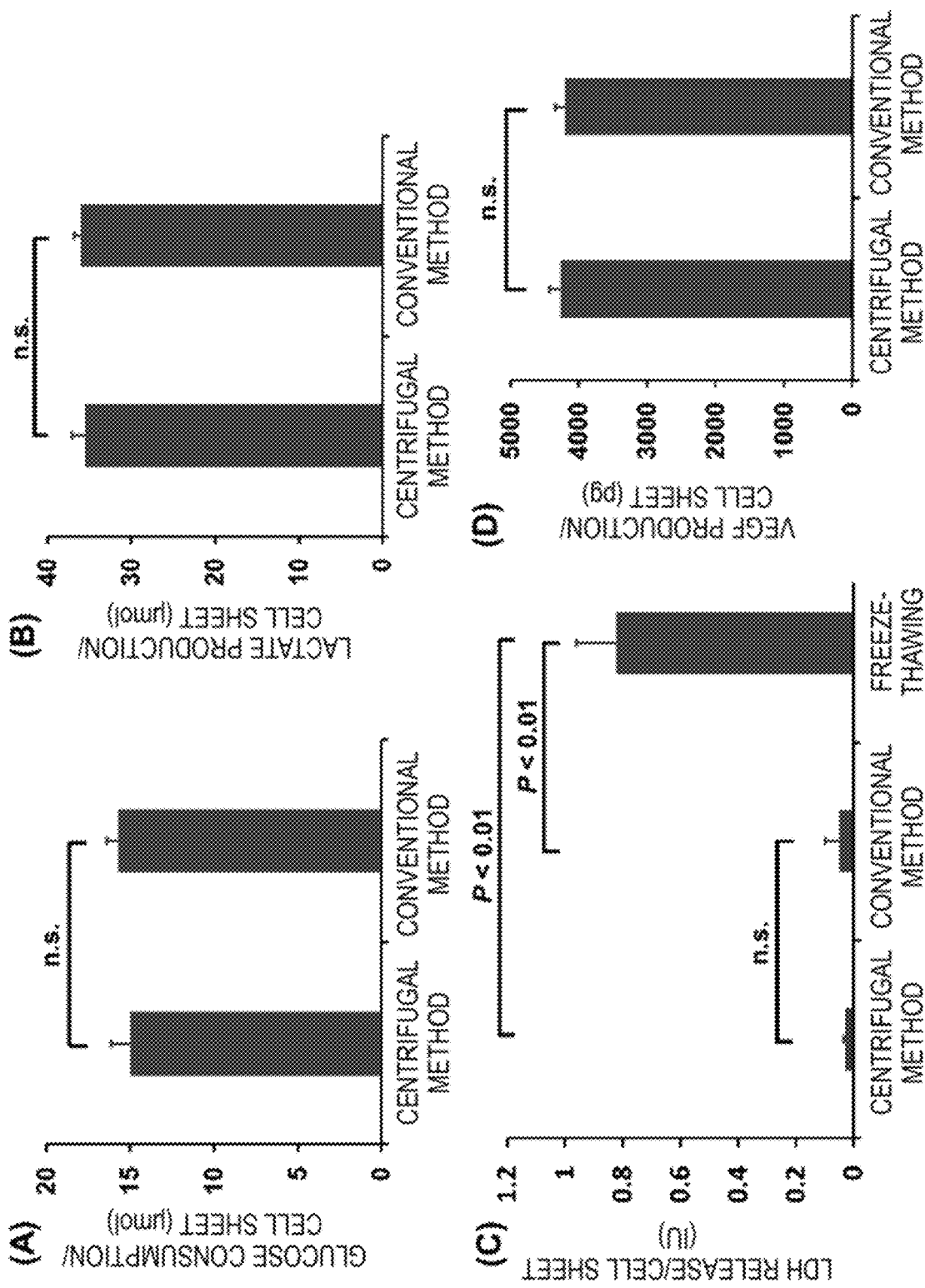
FIG. 5 illustrates an effect of an operation of applying centrifugal force on the activity of C2C12 myoblast cell sheet. A C2C12 cell sheet was treated with a centrifugal method (36-37° C., 55×g, 5 minutes) or a conventional method (incubation at 37° C. for 45 minutes) and incubated for 16 hours. (A) a glucose consumption, (B) a lactate production, (C) a lactate dehydrogenase (LDH) release, and (D) a vascular endothelial growth factor (VEGF) production after 16 hours of the incubation are shown. The freeze-thawing indicates an amount of LDH released from the cell sheet after subjecting a C2C12 cell sheet twice to freeze-thawing (positive control). n.s.: Not significant.

Example 3: Quantitative Evaluation of Glucose Consumption, Production of Lactate and VEGF, and LDH Release The effect of centrifugal force application on the C2C12 myoblast cell sheet was quantitatively evaluated by means of assays of (i) cell metabolism, (ii) LDH release, and (iii) cytokine production. It was revealed that the cell sheet swiftly adhered to the temperature-responsive culture surface actively consumes glucose and produces lactate, similarly to that obtained by the conventional method (non-centrifugation method) (the parts (A) and (B) of FIG. 5).

When the cell sheet was subjected to freezing-thawing treatment, release of a large amount of LDH was detected. On the other hand, in both the centrifugal method and the conventional method, release of only a very small amount was detected (the part (C) of FIG. 5). The cell sheet obtained by the centrifugal method caused VEGF production, similarly to the cell sheet obtained by the conventional method (the part (D) of FIG. 5). These results reveal that the cell sheet swiftly adhered to the culture surface by heating/centrifuging operation has the same function as that obtained by the time-consuming conventional method. In the experiment for analyzing cytotoxicity illustrated the part (C) of FIG. 5, the LDH release, i.e., the tissue toxicity, is very small, and a statistical difference was not observed in both of the centrifugal method and the conventional method. However, the tissue toxicity tended to be smaller, and the coefficient of variation thereof was remarkably low in the cell sheet rapidly adhered by centrifugal force application (centrifugal method: conventional method=18:104). This suggests that compared with the conventional method, the centrifugal method produces a small difference among samples and is suitable for producing a homogeneous tissue. The conventional method may slightly damage the cells since the culture medium is removed and then the cell sheet is cultured in a $CO_2$ incubator at 37° C. until adhesion. compared with the conventional method, the centrifugal method produces a small difference among samples and is suitable for producing a homogeneous tissue. The conventional method may slightly damage the cells since the culture medium is removed and then the cell sheet is cultured in a $CO_2$ incubator at 37° C. until adhesion.

Example 4: Cross-Sectional Observation of Layered C2C12 Myoblast Cell Sheets on Temperature-Responsive The adhesion (i) between the C2C12 myoblast cell sheet and the temperature-responsive culture surface and (ii) between layered cell sheets was observed in the cross-section by OCT. When the culture medium was removed, many spaces were observed between the C2C12 myoblast cell sheet and the temperature-responsive culture dish surface, but after centrifugal force application, substantially no space was detected (the parts (A) and (B) of FIG. 6).

Figure 6:
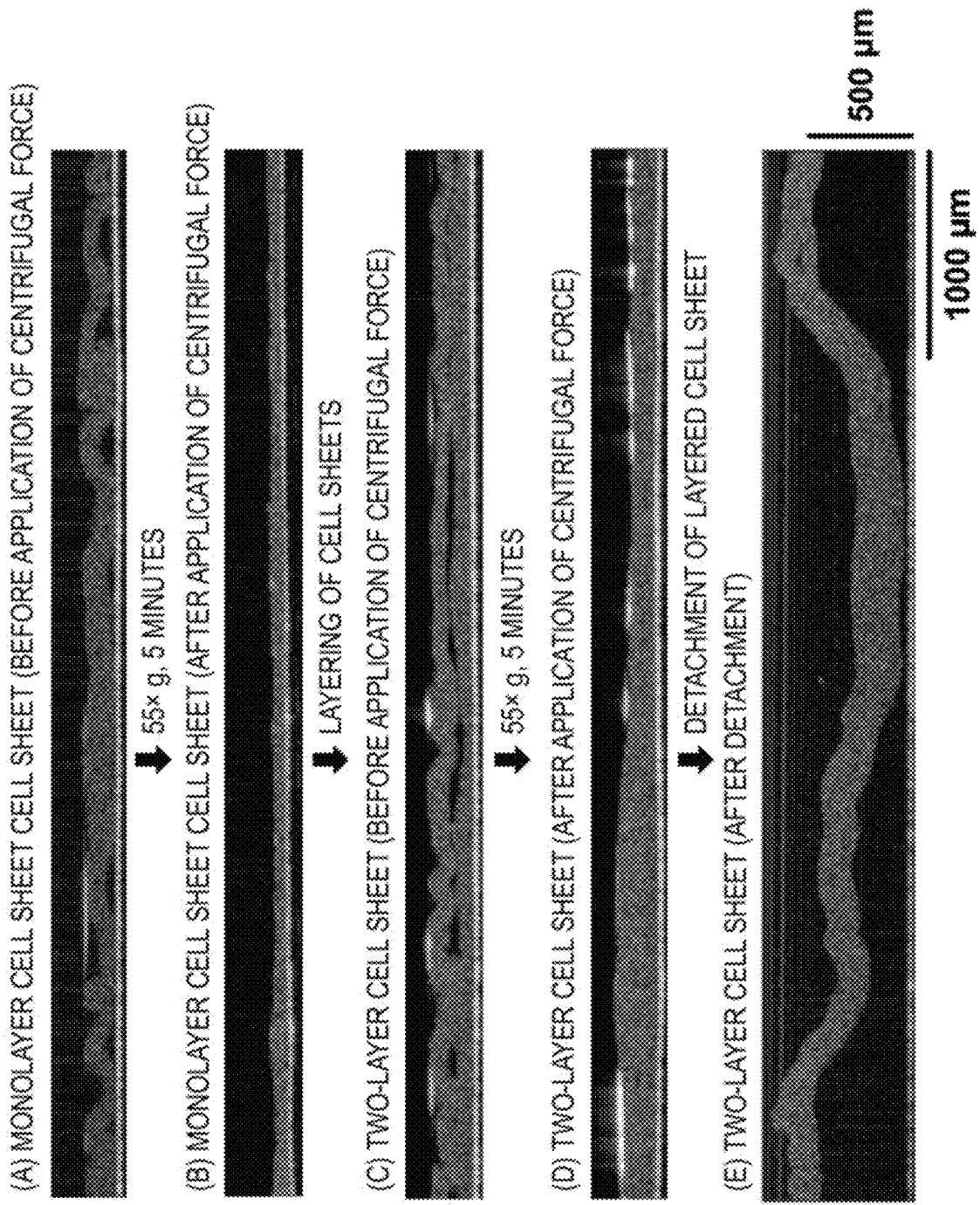
FIG. 6 illustrates a cross-section of a C2C12 myoblast cell sheet on a temperature-responsive culture surface, which is observed by optical coherence tomography (OCT). (A) and (B): Monolayer cell sheets (A) before and (B) after applying a centrifugal force (55×g, 5 minutes) at 36 to 37° C. (C) and (D): Two-layer cell sheets (C) before and (D) after applying a centrifugal force (55×g, 5 minutes) at 36 to 37° C. (E) A two-layer cell sheet after releasing from the cell culture surface.

When cell sheets were layered and the culture medium was then removed, many spaces were observed between layered cell sheets (the part (C) of FIG. 6). After centrifugal force application, the spaces were substantially not detected (the part (D) of FIG. 6). Three to five layers of cell sheets could be successfully layered by repeating the same operations. It could also be confirmed that the thickness of the tissue increases according to the number of cell sheets layered (the parts (A) to (C) of FIG. 5). Tight adhesion between layered cell sheets after centrifugal force application was observed in the cross-section by OCT.

Thereafter, the culture dish having the layered cell sheet was placed in a $CO_2$ incubator at 20° C. so as to release the layered cell sheet. After the release, tight adhesion between cell sheets layered was maintained (the part (E) of FIG. 6 (two-layer cell sheet) and the part (D) of FIG. 7 (five-layer cell sheet)).

Furthermore, the layered cell sheet could be manipulated without damage by using a cell sheet transfer device and could be easily and completely transferred to the target place. This indicates that the layered cell sheet obtained by the present invention can be easily transplanted on the target tissue.

It has been found that when the method of the present invention is used, the layered cell sheet (three-dimensional tissue) produced can be obtained non-invasively in a short time by only dropping the temperature. On the other hand, if the centrifugation is performed without heating even under optimal centrifugation conditions, the cell sheet is detached from the temperature-responsive culture dish with as high a frequency as 75%. This makes it difficult to produce a three-dimensional tissue on the temperature-responsive culture dish, and even if the layering is successful, second centrifugation causes slipping of layered cell sheet in some samples.

The present application is based on Japanese Patent Application No. 2017-127873 filed on Jun. 29, 2017, the contents of which are incorporated herein by way of reference.

INDUSTRIAL APPLICABILITY

The present invention simplifies the step of layering cell sheets, and can shorten the time of producing a layered cell sheet. In addition, based on the present invention, the layered cell sheet maintaining the morphology can be obtained reproducibly.

The invention claimed is:

1. A method for producing a layered cell sheet on a temperature-responsive culture surface, the method comprising:
   (1) a step of placing a first cell sheet on the temperature-responsive culture surface and applying a centrifugal force to the first cell sheet for a predetermined time in a temperature range from a lower critical solution temperature of the temperature-responsive culture surface to 45° C.,
   (2) a step of further placing a second cell sheet on the first cell sheet on the temperature-responsive culture surface, and
   (3) a step of applying a centrifugal force to the first cell sheet and the second cell sheet on the temperature-responsive culture surface for a predetermined time in the temperature range from the lower critical solution temperature to 45° C.,
   wherein the centrifugal force is applied by a centrifuge having a heating function.
2. The method according to claim 1, further comprising:
   (4) a step of repeating the steps (2) and (3) an arbitrary number of times.
3. The method according to claim 1, wherein the temperature-responsive culture surface is at least partially coated with poly(N-isopropylacrylamide).
4. The method according to claim 1, wherein the lower critical solution temperature is 32° C.
5. The method according to claim 1, wherein the temperature range is from 34 to 39° C.
6. The method according to claim 1, wherein the predetermined time in steps (1) and (3) is independently from 1 to 10 minutes.
7. The method according to claim 1, wherein the centrifugal force in steps (1) and (3) is independently from 25×g to 150×g.
8. The method according to claim 1, wherein a time until reaching the centrifugal force in steps (1) and (3) is independently from 15 to 60 seconds.
9. The method according to claim 1, wherein a time until ceasing the centrifugal force in steps (1) and (3) is independently from 15 to 60 seconds.
10. The method according to claim 1, wherein the first cell sheet and/or the second cell sheet contains one type of cells or two or more types of cells selected from the group consisting of cardiomyocytes, hepatocytes, fibroblasts, myoblasts, pancreatic cells, renal cells, vascular endothelial cells, and epithelial cells.
11. The method according to claim 1, further comprising:
   (5) a step of releasing a layered cell sheet from the temperature-responsive culture surface by exposing the temperature-responsive culture surface to a temperature less than the lower critical solution temperature.
12. The method according to claim 1, wherein the predetermined time of the step (3) is shorter than the predetermined time of the step (1).

* * * * *